(12) United States Patent
Dueva-Koganov et al.

(10) Patent No.: US 10,898,423 B2
(45) Date of Patent: Jan. 26, 2021

(54) SYNERGISTIC ANTIOXIDANT COMPOSITIONS

(71) Applicant: RODAN & FIELDS, LLC, San Francisco, CA (US)

(72) Inventors: Olga Dueva-Koganov, Emeryville, CA (US); Taylor Oswald, Oakland, CA (US); Christine Crane, Walnut Creek, CA (US); Robert Bianchini, Dana Point, CA (US)

(73) Assignee: RODAN & FIELDS, LLC, San Francisco, CA (US)

( * ) Notice: Subject to any disclaimer, the term of this patent is extended or adjusted under 35 U.S.C. 154(b) by 0 days.

(21) Appl. No.: 16/796,632

(22) Filed: Feb. 20, 2020

(65) Prior Publication Data

US 2020/0261344 A1 Aug. 20, 2020

Related U.S. Application Data (60) Provisional application No. 62/808,052, filed on Feb. 20, 2019.

(51) Int. Cl.
| | | |
|---|---|---|
| *A61K 8/60* | (2006.01) | |
| *A61K 8/37* | (2006.01) | |
| *A61Q 19/00* | (2006.01) | |
| *A61Q 19/08* | (2006.01) | |
| *A61K 8/58* | (2006.01) | |

(52) U.S. Cl.
CPC .............. *A61K 8/602* (2013.01); *A61K 8/375* (2013.01); *A61K 8/58* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| | | |
|---|---|---|
| 2006/0159714 A1 | 7/2006 | Thorel |
| 2010/0273729 A1 | 10/2010 | Park et al. |
| 2017/0156999 A1 | 6/2017 | Harris et al. |

FOREIGN PATENT DOCUMENTS

| | | |
|---|---|---|
| JP | 2017100993 A | 6/2017 |
| WO | 2014014271 A1 | 1/2014 |

OTHER PUBLICATIONS

Eggensperger, H., Wilker, M., & Bauer, P. (1998). Rosmarinic acid. A natural multiactive substance for cosmetics and dermatology. Part 2. Combinations of rosmarinic acid with other natural ingredients. SOFW Journal, 124(10), 634-636. (Year: 1998).*

Kojima-Yuasa, A., Hayashi, R., Han, L., Watanabe, B., Hiratake, J., & Matsui-Yuasa, I. (2012). A γ-glutamyl transpeptidase (GGT) inhibitor enhances collagen and elastin synthesis. J Jpn Cosmet Sci Soc, 36(2), 93-100. (Year: 2012).*

Brewer, "Natural Antioxidants: Sources, Compounds, Mechanisms of Action and Potential Applications", Jun. 14, 2011, Comprehensive Reviews in Food Science and Food Safety 10:221-247.

International Search Report and Written Opinion for PCT/US2020/019098 dated May 11, 2020.

Kamiyama et al., "Phosphonate-based Irreversible Inhibitors of Human γ-Glutamyl Transpeptidase (GGT). GGsTop is a Non-Toxic and Highly Selective Inhibitor With Critical Electrostatic Interaction With an Active-Site Residue Lys562 for Enhanced Inhibitory Activity", Aug. 31, 2016, Bioorganic and Medicinal Chemistry 24:5340-5352.

McMullen, "Antioxidants and the Skin", first edition published Jan. 20, 2013, Allured Books, Carol Stream, IL USA (abstract only).

\* cited by examiner

*Primary Examiner* — Dale R Miller
(74) *Attorney, Agent, or Firm* — Troutman Pepper Hamilton Sanders LLP (57) ABSTRACT

The antioxidant compositions of various embodiments comprise methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-β-D-glucopyranosyloxy]-4H-chromen-4-one, also known as rutin wherein the antioxidant composition demonstrate a synergistic effect compared with the MCAP, the rosmarinic acid, or the rutin alone. The methods include treating skin or hair damaged by reactive oxygen species, preventing skin or hair damage, and treating aged skin.

25 Claims, 9 Drawing Sheets

Overall Antioxidant Efficacy

Antiox A: MCAP
Antiox B: Rosmarinic acid
Antiox C: Rutin

Figure 5

Antiox A: MCAP
Antiox B: Rosmarinic acid
Antiox C: Rutin

Figure 6

Antiox A: MCAP
Antiox B: Rosmarinic acid
Antiox C: Rutin

Figure 7

Antiox A: MCAP
Antiox B: Rosmarinic acid
Antiox C: Rutin

Antiox A: MCAP
Antiox B: Rosmarinic acid
Antiox C: Rutin

SYNERGISTIC ANTIOXIDANT COMPOSITIONS

CROSS-REFERENCE TO RELATED APPLICATIONS

This application claims priority to U.S. Provisional Application No. 62/808,052 filed Feb. 20, 2019, which is incorporated herein by reference in its entirety.

SUMMARY

Embodiments disclosed herein are directed to antioxidant compositions comprising methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-β-D-glucopyranosyloxy]-4H-chromen-4-one, also known as rutin.

Embodiments are directed to methods of treating skin or hair damaged by reactive oxygen species in a subject in need thereof comprising topically administering to the skin of the subject an antioxidant composition comprising methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-β-D-glucopyranosyloxy]-4H-chromen-4-one, also known as rutin.

Embodiments are directed to methods of preventing skin or hair damage in a subject in need thereof comprising topically administering to the skin of the subject an antioxidant composition comprising methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-β-D-glucopyranosyloxy]-4H-chromen-4-one, also known as rutin.

Embodiments are directed to methods of treating aged skin in a subject in need thereof comprising topically administering to the skin of the subject an antioxidant composition comprising methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-β-D-glucopyranosyloxy]-4H-chromen-4-one, also known as rutin.

BRIEF DESCRIPTION OF THE DRAWINGS

For a fuller understanding of the nature and advantages of the present embodiments, reference should be made to the following detailed description taken in connection with the accompanying drawings, in which.

DETAILED DESCRIPTION

It is commonly held that exposure to external aggressors, such as UV radiation, air pollution, and cigarette smoke, results in increased signs of skin aging. Skin aging is a common concern for the general population, especially for women. Therefore, it is desirable to have an effective agent to prevent or treat the damage caused by the external aggressors.

One mechanism associated with this damage is explained by the generation of reactive oxygen species (ROS). ROS are chemically unstable agents generated via numerous sources, including exposure to sunlight and pollution, which cause damage to lipids, proteins, and DNA. This chemical damage results in collagen and elastin breakdown, slowed cell turnover, and increased melanocyte production, causing the skin to have a more aged appearance. Reactive oxygen species are also known to activate an inflammatory response which leads to MMP activation (i.e. collagen degradation) and melanin production, leading to damage, aged skin.

A topical agent capable of scavenging ROS generated by external factors may aid in decreasing ROS propagation and, therefore, minimize skin damage.

Antioxidants have demonstrated the ability to mitigate skin damage caused by ROS when topically applied. Many mechanisms exist for antioxidants, and antioxidants vary in function and efficacy.

Accordingly, creation of an antioxidant composition targeting multiple pathways may more effectively function to slow the development of skin damage caused by ROS-mediated pathways and to contribute to overall environmental protection compared with targeting a single pathway alone.

Kyoto molecule, formally known as Nahlsgen with chemical name methyl carboxymethylphenylaminocarboxy propylphosphonate ("MCAP"), is an inhibitor of gamma-glutamyltranspeptidase (GGT) and functions to control cell redox status. Rosmarinic acid, a phenolic acid, structurally functions to trap free radicals and inhibit lipid oxidation. Rutin is a flavonoid that functions to chelate metal ions and scavenges free radicals. Accordingly, this novel blend of antioxidants targets multiple pathways, including inhibition of gamma-glutamyltranspeptidase (GGT) to control cell redox status, structural trapping of free radicals, inhibition of lipid oxidation, chelation of metal ions, and scavenging of free radicals.

Embodiments described herein are directed to an antioxidant composition of MCAP, rosmarinic acid, and rutin that act synergistically to effectively treat and/or prevent the skin damage caused by exposure to external aggressors, such as UV radiation.

Various aspects will be described in detail hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 wt % to 8 wt % is stated, it is intended that 2 wt %, 3 wt %, 4 wt %, 5 wt %, 6 wt %, and 7 wt % are also explicitly disclosed, as well as the range of values greater than or equal to 1 wt % and the range of values less than or equal to 8 wt %.

All percentages, parts and ratios are based upon the total weight of the formulations and compositions and all measurements made are at about 25° C., unless otherwise specified.

The singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

The word "about" when immediately preceding a numerical value means a range of plus or minus 10% of that value, e.g, "about 50" means 45 to 55, "about 25,000" means 22,500 to 27,500, etc, unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g, more than 49.5 to less than 52.5. Furthermore, the phrases "less than about" a value or "greater than about" a value should be understood in view of the definition of the term "about" provided herein.

The terms "administer," "administering" and "administration" as used herein refer to either directly administering a compound (also referred to as an agent of interest) or pharmaceutically acceptable salt of the compound (agent of interest) or a composition to a subject.

The transitional term "comprising," which is synonymous with "including," "containing," or "characterized by," is inclusive or open-ended and does not exclude additional, un-recited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed subject matter. In some embodiments or claims where the term comprising is used as the transition phrase, such embodiments can also be envisioned with replacement of the term "comprising" with the terms "consisting of" or "consisting essentially of."

The term "cosmetic" means an agent utilized, and/or intended to be applied to the human body for cleansing, beautifying, promoting attractiveness, altering the appearance of the skin or any combination thereof.

The phrase "pharmaceutically acceptable" or "cosmetically acceptable" is employed herein to refer to those agents of interest/compounds, salts, compositions, dosage forms, etc, which are within the scope of sound medical judgment suitable for use in contact with the tissues of human beings and/or other mammals without excessive toxicity, irritation, allergic response, or other problem or complication, commensurate with a reasonable benefit/risk ratio. In some aspects, pharmaceutically acceptable means approved by a regulatory agency of the federal or a state government, or listed in the U.S. Pharmacopeia or other generally recognized pharmacopeia for use in mammals (e.g, animals), and more particularly, in humans.

The terms "patient" and "subject" are interchangeable and may be taken to mean any living organism which may be treated with compounds or compositions provided for herein. As such, the terms "patient" and "subject" may comprise, but is not limited to, any non-human mammal, primate or human. In some embodiments, the patient or subject is an adult, child, or infant. In some embodiments, the patient or subject is a human.

The term "composition" as used herein refers to a combination or a mixture of two or more different ingredients, components, or substances; e.g., a combination of antioxidants.

The term "inhibitor" or "enzyme inhibitor" as used herein refers to a molecule that binds to an enzyme and decreases its activity. Since blocking an enzyme's activity can kill a pathogen or correct a metabolic imbalance, many drugs are enzyme inhibitors The term "gamma-glutamyltranspeptidase" ("GGT") as used herein refers to a transferase (a type of enzyme) that catalyzes the transfer of gamma-glutamyl functional groups from molecules such as glutathione to an acceptor that may be an amino acid, a peptide or water.

The term "reactive oxygen species" ("ROS") as used herein refer to chemically unstable agents containing oxygen generated via numerous sources, including exposure to sunlight and pollution, which cause damage to lipids, proteins, and DNA. Examples of ROS comprise peroxides, superoxide, hydroxyl radical, singlet oxygen, and alpha-oxygen.

The terms "topically" and "topical" as used herein refer to application of the compositions to the surface of the skin, mucosal cells, keratins and tissues. Examples of keratins are nails and hair.

The term "treating" as used herein refers to methods of treating a skin disorder or a systemic condition, and generally includes the administration of a compound or composition which reduces the frequency of, or delays the onset of, symptoms of a medical condition or enhance the texture, appearance, color, sensation, or hydration of the intended tissue treatment area of the tissue surface in a subject relative to a subject not receiving the compound or composition. This can include reversing, reducing, or arresting the symptoms, clinical signs, and underlying pathology of a condition in a manner to improve or stabilize a subject's condition.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason. Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Compositions

Embodiments disclosed herein are directed to antioxidant compositions comprising methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-β-D-glucopyranosyloxy]-4H-chromen-4-one, also known as rutin.

In some embodiments, the antioxidant composition demonstrates a synergistic effect compared with the MCAP, the rosmarinic acid, or the rutin alone, or a combination of two of such compounds.

In some embodiments, the amount of MCAP in the antioxidant composition is present in an amount of about 1.0 wt. % to about 5.0 wt. %. In some embodiments, the amount of MCAP in the antioxidant composition is present in an amount of less than about 1.0 wt. %. In some embodiments, the amount of MCAP in the antioxidant composition is present in an amount of about 0.0003 wt. % to about 1.0 wt. %. In some embodiments, the amount of MCAP in the antioxidant composition is present in an amount of about 0.003 wt. % to about 1.0 wt. %. In some embodiments, the amount of MCAP in the antioxidant composition is present in an amount of about 0.03 wt. % to about 1.0 wt. %. In some embodiments, the amount of MCAP in the antioxidant composition is present in an amount of about 0.000003 wt. % to about 0.0003 wt. %. In some embodiments, the amount of MCAP in the antioxidant composition is present in an amount of about 0.00003 wt. % to about 0.003 wt. %. In some embodiments, the amount of MCAP in the antioxidant composition is present in an amount of about 0.0003 wt. % to about 0.03 wt. %. In some embodiments, the amount of MCAP in the antioxidant composition is present in an amount of about 0.003 wt. % to about 0.3 wt. %. In some embodiments, the amount of MCAP in the antioxidant composition is present in an amount of about 0.001 wt. % to about 0.002 wt. %. In some embodiments, the amount of MCAP in the antioxidant composition is present in an amount of about 0.000003 wt. % to about 0.003 wt. %. In some embodiments, the amount of MCAP in the antioxidant composition is present in an amount of about 0.000003 wt. % to about 0.0003 wt. %. In some embodiments, the amount of MCAP in the antioxidant composition is present in an amount of about 0.000003 wt. % to about 0.00003 wt. %. In some embodiments, the amount of MCAP in the antioxidant composition is present in an amount of about 0.000001 wt. % to about 1.0 wt. %. In some embodiments, the amount of MCAP in the antioxidant composition is present in an amount of about 0.000001 wt. % to about 0.1 wt. %. In some embodiments, the amount of MCAP in the antioxidant composition is present in an amount of about 0.000001 wt. % to about 0.01 wt. %. In some embodiments, the amount of MCAP in the antioxidant composition is present in an amount of about 0.000001 wt. % to about 0.001 wt. %. In some embodiments, the amount of MCAP in the antioxidant composition is present in an amount of about 0.000001 wt. % to about 0.0001 wt. %.

In some embodiments, the amount of rosmarinic acid in the antioxidant composition is present in an amount of about 1.0 wt. % to about 5.0 wt. %. In some embodiments, the amount of rosmarinic acid in the antioxidant composition is present in an amount of less than about 1.0 wt. %. In some embodiments, the amount of rosmarinic acid in the antioxidant composition is present in an amount of about 0.0003 wt. % to about 1.0 wt. %. In some embodiments, the amount of rosmarinic acid in the antioxidant composition is present in an amount of about 0.003 wt. % to about 1.0 wt. %. In some embodiments, the amount of rosmarinic acid in the antioxidant composition is present in an amount of about 0.03 wt. % to about 1.0 wt. %. In some embodiments, the amount of rosmarinic acid in the antioxidant composition is present in an amount of about 0.0003 wt. % to about 0.03 wt. %. In some embodiments, the amount of rosmarinic acid in the antioxidant composition is present in an amount of about 0.003 wt. % to about 0.03 wt. %. In some embodiments, the amount of rosmarininc acid in the antioxidant composition is present in an amount of about 0.001 wt. % to about 0.002 wt. %. In some embodiments, the amount of rosmarinic acid in the antioxidant composition is present in an amount of about 0.0003 wt. % to about 0.003 wt. %. In some embodiments, the amount of rosmarinic acid in the antioxidant composition is present in an amount of about 0.0001 wt. % to about 1.0 wt. %. In some embodiments, the amount of rosmarinic acid in the antioxidant composition is present in an amount of about 0.001 wt. % to about 1.0 wt. %. In some embodiments, the amount of rosmarinic acid in the antioxidant composition is present in an amount of about 0.01 wt. % to about 1.0 wt. %. In some embodiments, the amount of rosmarinic acid in the antioxidant composition is present in an amount of about 0.1 wt. % to about 1.0 wt. %. In some embodiments, the amount of rosmarinic acid in the antioxidant composition is present in an amount of about 0.0001 wt. % to about 0.1 wt. %. In some embodiments, the amount of rosmarinic acid in the antioxidant composition is present in an amount of about 0.0001 wt. % to about 0.01 wt. %. In some embodiments, the amount of rosmarinic acid in the antioxidant composition is present in an amount of about 0.0001 wt. % to about 0.001 wt. %.

In some embodiments, the amount of rutin in the antioxidant composition is present in an amount of about 1.0 wt. % to about 5.0 wt. %. In some embodiments, the amount of rutin in the antioxidant composition is present in an amount of less than about 1.0 wt. %. In some embodiments, the amount of rutin in the antioxidant composition is present in an amount of about 0.0003 wt. % to about 1.0 wt. %. In some embodiments, the amount of rutin in the antioxidant composition is present in an amount of about 0.003 wt. % to about 1.0 wt. %. In some embodiments, the amount of rutin in the antioxidant composition is present in an amount of about 0.03 wt. % to about 1.0 wt. %. In some embodiments, the amount of rutin in the antioxidant composition is present in an amount of about 0.0003 wt. % to about 0.03 wt. %. In some embodiments, the amount of rutin in the antioxidant composition is present in an amount of about 0.003 wt. % to about 0.03 wt. %. In some embodiments, the amount of rutin in the antioxidant composition is present in an amount of about 0.001 wt. % to about 0.002 wt. %. In some embodiments, the amount of rutin in the antioxidant composition is present in an amount of about 0.0003 wt. % to about 0.003 wt. %. In some embodiments, the amount of rutin in the antioxidant composition is present in an amount of about 0.0001 wt. % to about 1.0 wt. %. In some embodiments, the amount of rutin in the antioxidant composition is present in an amount of about 0.001 wt. % to about 1.0 wt. %. In some embodiments, the amount of rutin in the antioxidant composition is present in an amount of about 0.01 wt. % to about 1.0 wt. %. In some embodiments, the amount of rutin in the antioxidant composition is present in an amount of about 0.1 wt. % to about 1.0 wt. %. In some embodiments, the amount of rutin in the antioxidant composition is present in an amount of about 0.0001 wt. % to about 0.1 wt. %. In some embodiments, the amount of rutin in the antioxidant composition is present in an amount of about 0.0001 wt. % to about 0.01 wt. %. In some embodiments, the amount of rutin in the antioxidant composition is present in an amount of about 0.0001 wt. % to about 0.001 wt. %.

In some embodiments, the ratio of the MCAP:the rutin in the antioxidant composition is in a range of about 1:100 to about 1:1. In some embodiments, the ratio of the MCAP:the rosmarinic acid in the antioxidant composition is in a range of about 1:100 to about 1:1. In some embodiments, the ratio of the rosmarinic acid:the rutin in the antioxidant composition is in a range of about 1:100 to about 1:1. In some embodiments, the ratio of the MCAP:the rosmarinic acid:the rutin in the antioxidant composition is in a range of about 1:100:100 to about 1:1:1. In some embodiments, the ratio of the MCAP:the rosmarinic acid: the rutin in the antioxidant composition is 1:1:1.

In some embodiments, the antioxidant composition is a pharmaceutically acceptable excipient. In some embodiments, the pharmaceutically acceptable excipient is a topical formulation. In some embodiments, the topical formulation further comprises a solvent.

In some embodiments, the solvent is selected from the group consisting of pentylene glycol, butylene glycol, water, glycols, propylene glycol, isopropylene glycol, Coco-caprylate/caprate, 1,2-hexanediol, ethanol, and combinations thereof.

In some embodiments, the antioxidant composition is formulated into a topical formulation. In some embodiments, the antioxidant composition is present in the topical formulation at about 0.000001 wt. % to about 5.0 wt. %. In some embodiments, the antioxidant composition is present in a topical formulation at about 0.1 wt. % to about 5.0 wt. %. In some embodiments, the antioxidant composition is present in a topical formulation at about 0.01% to about 1.0%.

In some embodiments, the amount of MCAP present in the topical formulation is in an amount of about 0.000001 wt. % to about 5.0 wt. %. In some embodiments, the amount of MCAP present in the topical formulation is in an amount of about 0.001 wt. % to about 1.0 wt. %. In some embodiments, the amount of MCAP present in the topical formulation is in an amount of about 0.01 wt. % to about 0.1 wt. %. In some embodiments, the amount of MCAP present in the topical formulation is in an amount of about 0.0001 wt. % to about 0.01 wt. %. In some embodiments, the amount of MCAP present in the topical formulation is in an amount of less than about 0.01 wt. %. In some embodiments, the amount of MCAP present in the topical formulation is in an amount of less than about 0.1 wt. %. In some embodiments, the amount of MCAP present in the topical formulation is in an amount of less than about 1.0 wt. %.

In some embodiments, the amount of rosmarinic acid present in the topical formulation is in an amount of about 0.0001 wt. % to about 5.0 wt. %. In some embodiments, the amount of rosmarinic acid present in the topical formulation is in an amount of about 0.001 wt. % to about 1.0 wt. %. In some embodiments, the amount of rosmarinic acid present in the topical formulation is in an amount of about 0.01 wt. % to about 0.1 wt. %. In some embodiments, the amount of rosmarinic acid present in the topical formulation is in an amount of less than about 0.01 wt. %. In some embodiments, the amount of rosmarinic acid present in the topical formulation is in an amount of less than about 0.1 wt. %. In some embodiments, the amount of rosmarinic acid present in the topical formulation is in an amount of less than about 1.0 wt. %.

In some embodiments, the amount of rutin present in the topical formulation is in an amount of about 0.0001 wt. % to about 5.0 wt. %. In some embodiments, the amount of rutin present in the topical formulation is in an amount of about 0.001 wt. % to about 1.0 wt. %. In some embodiments, the amount of rutin present in the topical formulation is in an amount of about 0.01 wt. % to about 0.1 wt. %. In some embodiments, the amount of rutin present in the topical formulation is in an amount of less than about 0.01 wt. %. In some embodiments, the amount of rutin present in the topical formulation is in an amount of less than about 0.1 wt. %. In some embodiments, the amount of rutin present in the topical formulation is in an amount of less than about 1.0 wt. %.

In some embodiments, the ratio of the MCAP:the rutin in the topical formulation is in a range of about 1:100 to about 1:1. In some embodiments, the ratio of the MCAP:the rosmarinic acid in the topical formulation is in a range of about 1:100 to about 1:1. In some embodiments, the ratio of the rosmarinic acid:the rutin in the topical formulation is in a range of about 1:100 to about 1:1. In some embodiments, the ratio of the MCAP:the rosmarinic acid:the rutin in the topical formulation is in a range of about 1:100:100 to about 1:1:1. In some embodiments, the ratio of the MCAP:the rosmarinic acid: the rutin in the topical formulation is 1:1:1.

In some embodiments, the synergistic effect is an increase in absorbance of light at 250-400 nm. In some embodiments, the synergistic effect is a hyperchromic shift, a hypsochromic shift, or a bathochromic shift. In some embodiments, the total amount of the increased absorbance is significantly more than the absorbance of any of the MCAP, the rosmarinic acid, the rutin alone. In some embodiments, the increase is statistically significant.

In some embodiments, the topical formulation further comprises a pharmaceutical additive, a cosmetic additive, water, or combinations thereof.

In some embodiments, the pharmaceutical additive is selected from the group consisting of diluents, fillers, disintegrants, binders, lubricants, surfactants, hydrophobic vehicles, water soluble vehicles, emulsifiers, buffers, humectants, moisturizers, solubilizers, preservatives, colorants, plasticizers, carriers, excipients, and combinations thereof.

In some embodiments, the cosmetic additive is selected from the group consisting of vitamins, cosmetic peptides, oil control agents, sensation modifying agents, skin lightening agents, hydrating formulations, a sunblock agent, a compound that absorbs or reflects UV photons, other skin care agent and combinations thereof.

In some embodiments, the topical formulation is formulated in a form selected from the group consisting of a solution, fluid, emulsion, suspension, solid, semi-solid, jelly, paste, gel, hydrogel, ointment, lotion, cream, foam, mousse, liquid, spray, suspension, dispersion, powder, aerosol, or transdermal patches formulated as a liquid, cream, ointment, gel, or aerosol.

In some embodiments, the antioxidant composition is part of an anti-aging regimen. In some embodiments, the antioxidant composition is part of regimen for after sun care. In some embodiments, the antioxidant composition is part of a photoprotective regimen. In some embodiments, the photoprotective regimen is a sunblock regimen or a sunscreen. In some embodiments, the antioxidant composition is part of regimen for skin lightening. In some embodiments, the antioxidant composition is part of regimen for skin brightening. In some embodiments, the antioxidant composition is part of regimen for acne treatment. In some embodiments, the antioxidant composition is part of regimen for inflammation treatment. In some embodiments, the antioxidant composition is part of a color cosmetic regimen. In some embodiments, the antioxidant composition is part of a hair treatment regimen. In some embodiments, the antioxidant composition is part of a scalp treatment regimen.

A wide variety of methods may be used for preparing the compositions described herein. Broadly speaking, the compositions may be prepared by combining the components of the formulation, as described herein, at a temperature and for a time sufficient to provide a pharmaceutically acceptable composition. In embodiments described herein, MCAP, rosmarinic acid, and rutin are mixed with constant heating. In embodiments described herein, MCAP, rosmarinic acid, and rutin are mixed with are blended and pre-mixed with the solvent and then added to the water phase with agitation and heated. In certain embodiments, the mixture of MCAP, rosmarinic acid, and rutin are heated to about 30° C. to about 75° C., about 30° C. to about 60° C., about 30° C. to about 50° C., about 40° to about 75° C., about 50° C. to about 75° C., about 60° C. to about 75° C., or to about 40° C.

Methods of Using Compositions Described Herein

Embodiments are directed to methods of treating skin damaged by reactive oxygen species in a subject in need thereof comprising topically administering to the skin of the subject an antioxidant composition comprising methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-β-D-glucopyranosyloxy]-4H-chromen-4-one, also known as rutin.

Embodiments are directed to methods of treating hair damaged by reactive oxygen species in a subject in need thereof comprising topically administering to the skin of the subject an antioxidant composition comprising methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-β-D-glucopyranosyloxy]-4H-chromen-4-one, also known as rutin.

Embodiments are directed to methods of preventing skin damage in a subject in need thereof comprising topically administering to the skin of the subject an antioxidant composition comprising methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-→D-glucopyranosyloxy]-4H-chromen-4-one, also known as rutin.

Embodiments are directed to methods of preventing hair damage in a subject in need thereof comprising topically administering to the hair of the subject an antioxidant composition comprising methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-β-D-glucopyranosyloxy]-4H-chromen-4-one, also known as rutin.

Embodiments are directed to methods of treating aged skin in a subject in need thereof comprising topically administering to the skin of the subject an antioxidant composition comprising methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-β-D-glucopyranosyloxy]-4H-chromen-4-one, also known as rutin.

Embodiments are directed to methods of improving the appearance of the skin in a subject in need thereof comprising topically administering to the skin of the subject an antioxidant composition comprising methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-β-D-glucopyranosyloxy]-4H-chromen-4-one, also known as rutin.

Embodiments are directed to methods of improving the appearance of the hair in a subject in need thereof comprising topically administering to the skin of the subject an antioxidant composition comprising methyl carboxymethylphenylaminocarboxy propylphosphonate, also known as MCAP, (2R)-3-(3,4-dihydroxyphenyl)-2-{[(2E)-3-(3,4-dihydroxyphenyl)prop-2-enoyl]oxy}propanoic acid, also known as rosmarinic acid, and 2-(3,4-dihydroxyphenyl)-5,7-dihydroxy-3-[α-L-rhamnopyranosyl-(1→6)-β-D-glucopyranosyloxy]-4H-chromen-4-one, also known as rutin.

In embodiments described herein, the antioxidant composition demonstrates a synergistic effect compared with the MCAP, the rosmarinic acid, or the rutin alone.

In embodiments described herein, the antioxidant composition prevents the generation of reactive oxygen species in the skin or hair. In embodiments described herein, the antioxidant composition mitigates the generation of reactive oxygen species in the skin or hair.

In embodiments described herein, the reactive oxygen species is generated by UV radiation, pollution, heating, or combinations thereof.

In embodiments described herein, the skin damage is damage to lipids, proteins, DNA, or combinations thereof. In embodiments described herein, the hair damage is damage to lipids, proteins, DNA, or combinations thereof.

In embodiments described herein, the treatment of the aged skin results in improvement in a characteristic of the skin.

In embodiments described herein, the characteristic of the skin is selected from the group consisting of firmness, elasticity, fine lines, wrinkles, skin texture, skin tone, appearance, and any combination thereof.

In embodiments described herein, improving the appearance of the skin results in smoother skin, firmer skin, softer skin, brighter complexion, improved texture of the skin, even-looking skin, improvement of discoloration, disappearance of blemishes, decreased redness, or younger-looking skin. In some embodiments, improving the appearance of the skin results in an anti-inflammatory effect. In some embodiments, improving the appearance of the skin results in an increase in elasticity of the skin, a decrease in the fine lines of the skin, a decrease in the wrinkles of the skin, a more consistent skin tone, and any combination thereof.

In embodiments described herein, the treatment of the hair results in improvement in a characteristic of the hair.

In embodiments described herein, the characteristic of the hair is selected from the group consisting of shine, texture, fullness, smoothness, density, and combinations thereof.

In embodiments described herein, improving the appearance of the hair results in smoother hair, softer hair, brighter hair, improved texture of the hair, shiner hair, fuller hair, or more vibrant hair.

In embodiments described herein, the subject is an infant, a child, an adolescent, or an adult.

In embodiments described herein, the antioxidant composition is formulated as a topical formulation for anti-aging, after sun care, skin lightening, skin brightening, acne treatment, inflammation treatment, hair treatment, or scalp treatment.

In embodiments described herein, the antioxidant composition is formulated as a sunblock. In some embodiments, the antioxidant composition is formulated as an anti-aging regimen. In some embodiments, the antioxidant composition is formulated as an after sun care product. In some embodiments, the antioxidant composition is formulated as a photoprotective regimen. In some embodiments, the photoprotective regimen is a sunblock regimen or a sunscreen. In some embodiments, the antioxidant composition is formulated as a skin lightening product. In some embodiments, the antioxidant composition is formulated as a skin brightening product. In some embodiments, the antioxidant composition is formulated as an acne treatment. In some embodiments, the antioxidant composition is formulated as an inflammation treatment. In some embodiments, the antioxidant composition is formulated as a color cosmetic regimen. In some embodiments, the antioxidant composition is formulated as a hair treatment regimen. In some embodiments, the antioxidant composition is formulated as a scalp treatment regimen.

The subject matter is now described with reference to the following examples. These examples are provided for the purpose of illustration only and the claims should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLES

Using a Design of Experiment (DOE) approach according to Method E, three known antioxidants were tested for potential synergies in various antioxidant assays. Kyoto molecule, formally known as Nahlsgen with chemical name methyl carboxymethylphenylaminocarboxy propylphosphonate ("MCAP"), is an inhibitor of gamma-glutamyltranspeptidase (GGT) and functions to control cell redox status. Rosmarinic acid, a phenolic acid, structurally functions to trap free radicals and inhibit lipid oxidation. Rutin is a flavonoid that functions to chelate metal ions and scavenge free radicals.

Figure 1:
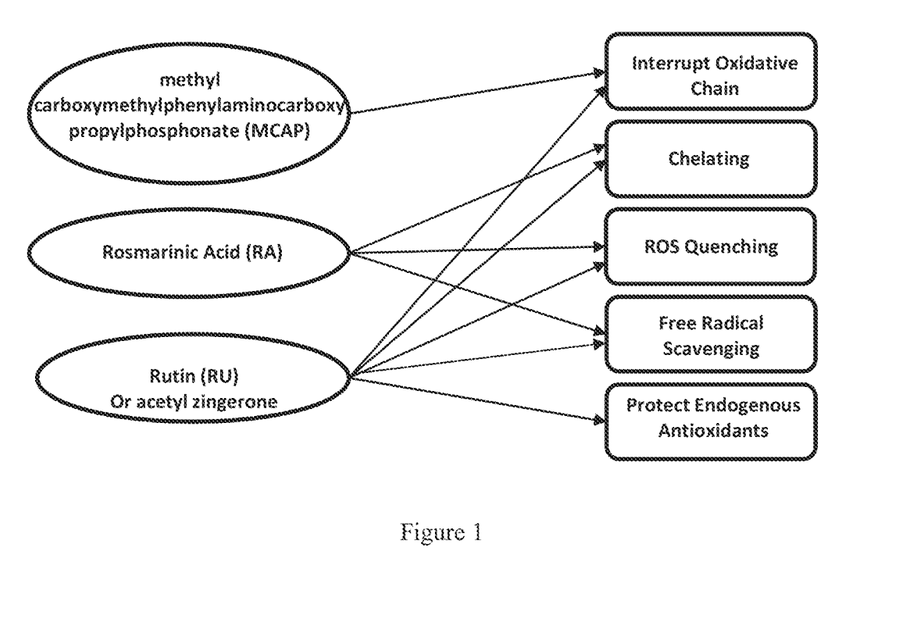
FIG. 1: Representation of antioxidants tested and pathways in which individual components are known to function.
Figure 2:
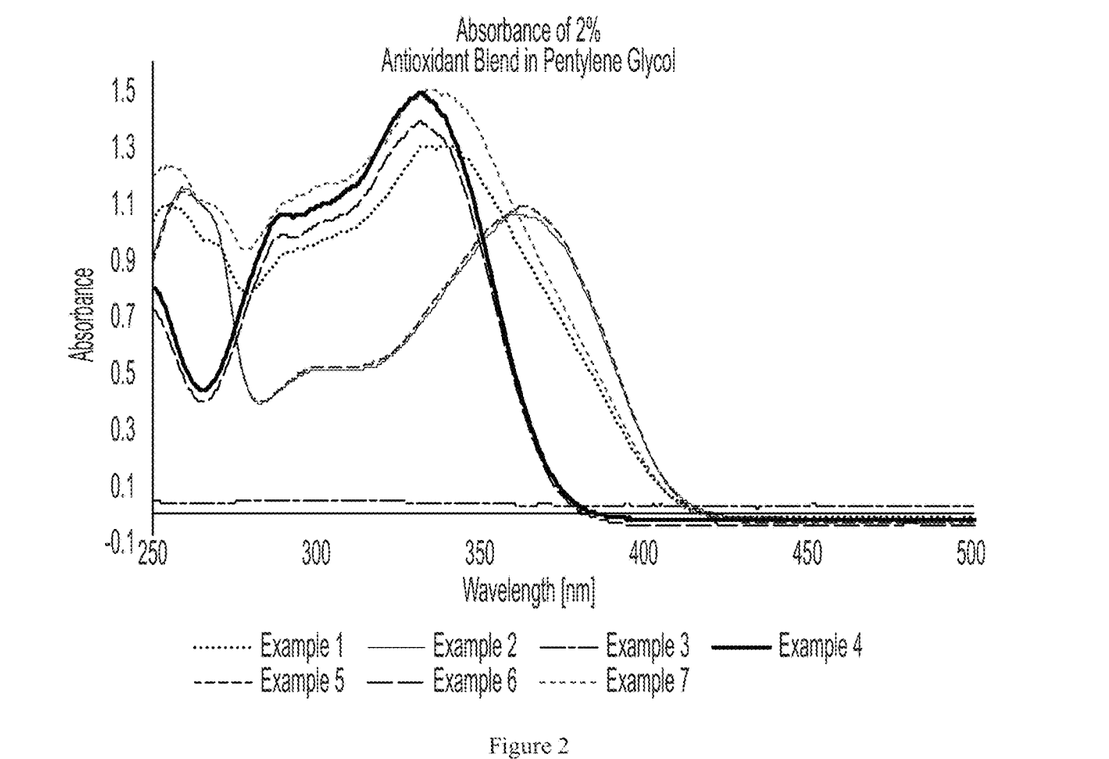
FIG. 2: Light absorbance of 2% of antioxidant compositions Ex1-Ex8 in pentylene glycol from 250 nm to 500 nm under the Ocean Optics UV is Spectrometer.
Figure 3:
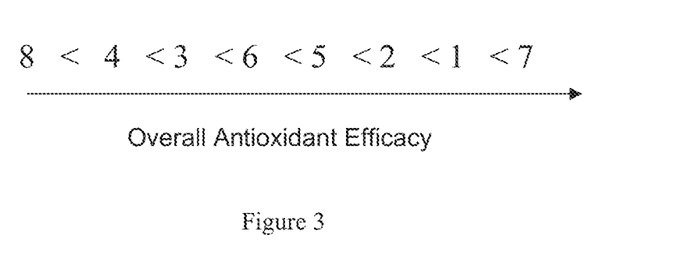
FIG. 3: Overall ranking of experimental antioxidant compositions Ex1-Ex8 based on comprehensive analysis of assays designed to tests multiple targets.
Figure 4:
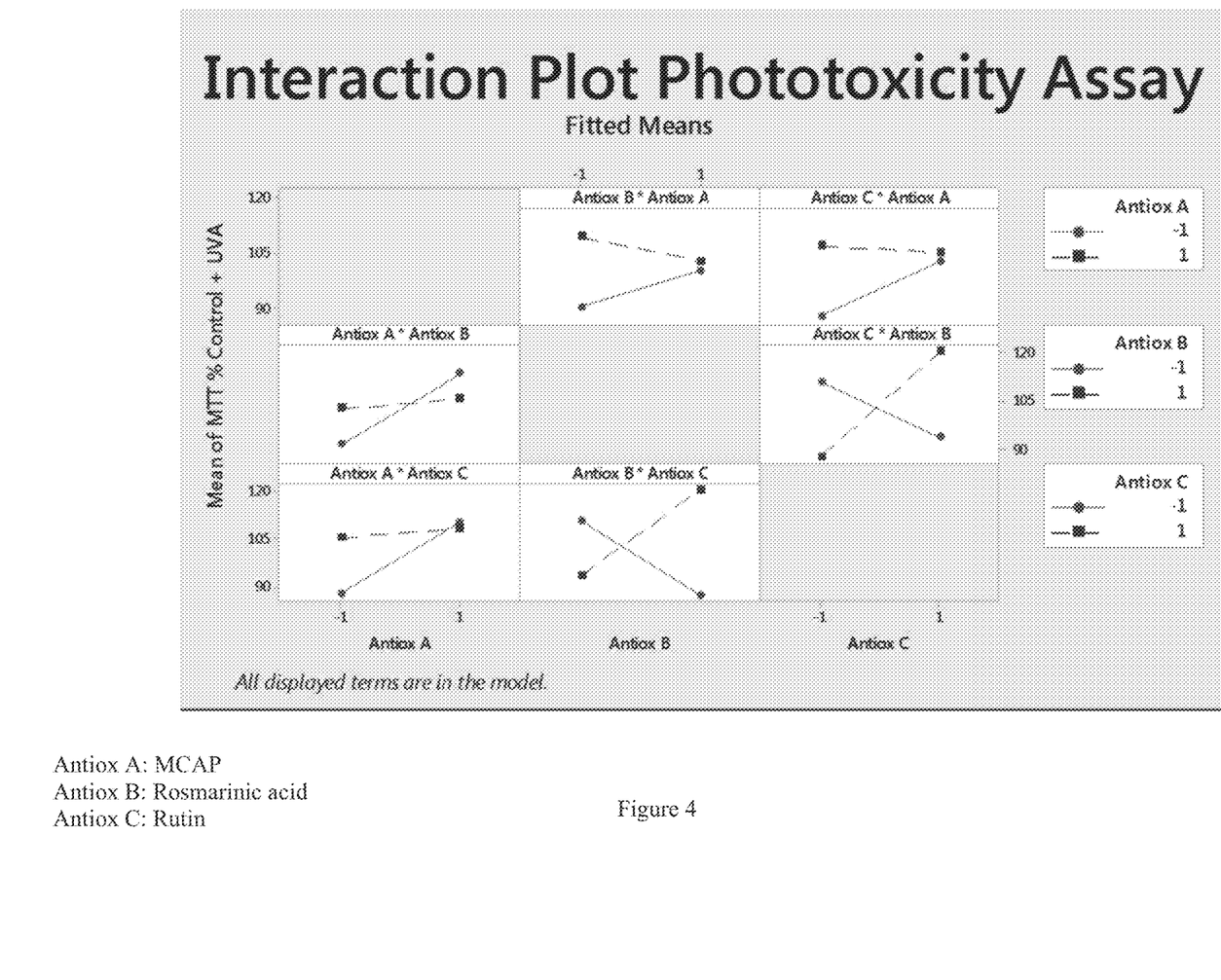
FIG. 4: Interaction plots for phototoxicity assay.
Figure 5:
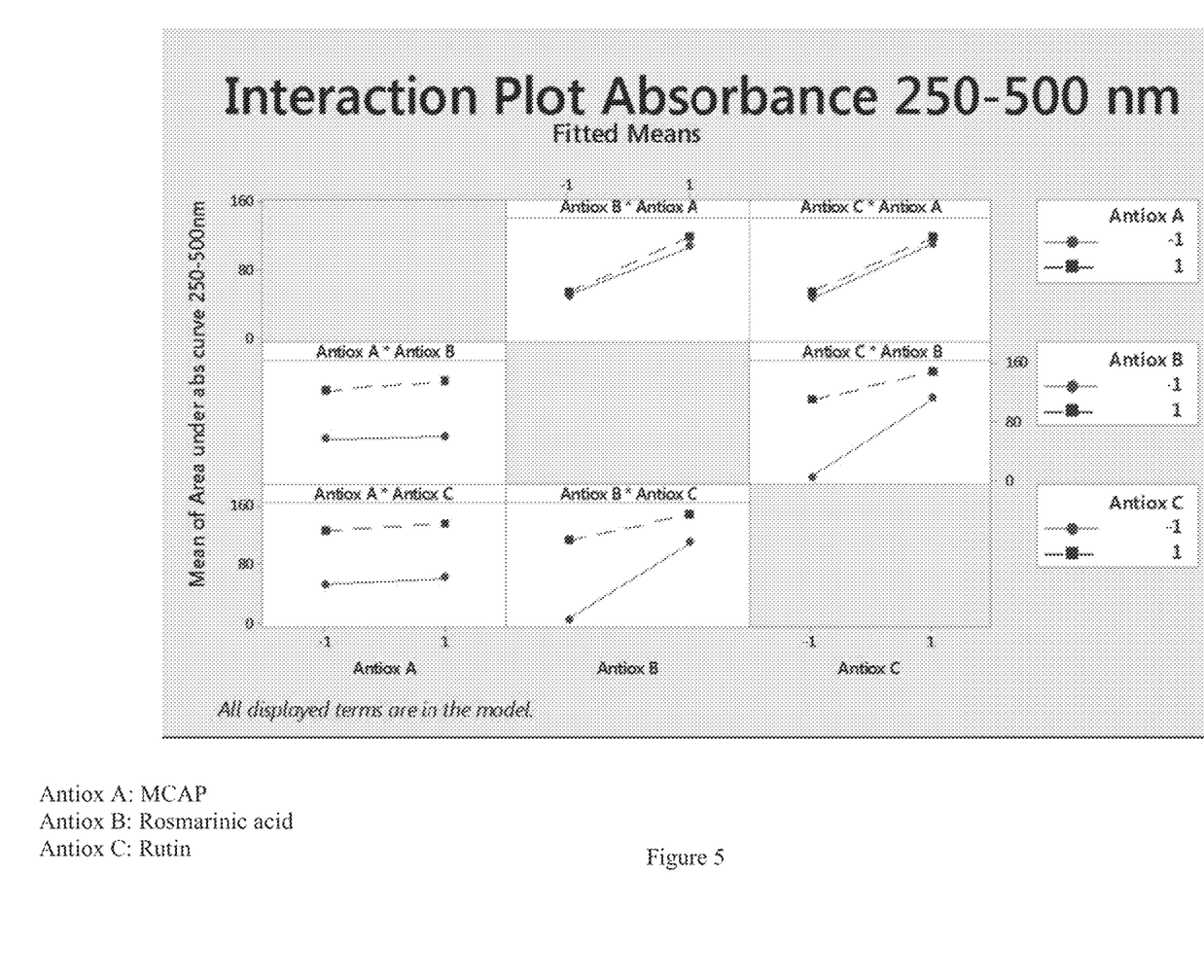
FIG. 5: Interaction plots for light absorbance assay at 250-500 nm.
Figure 6:
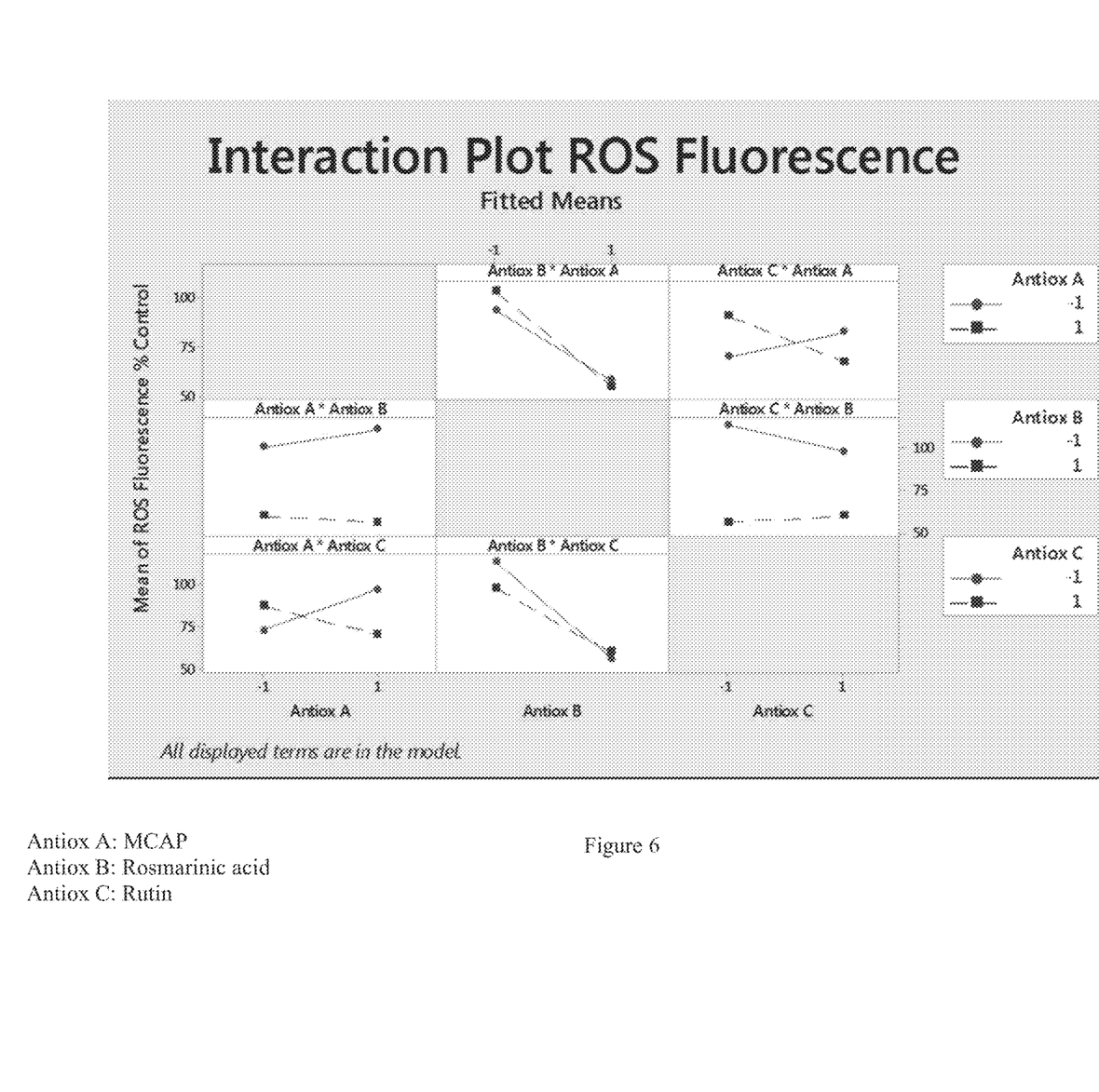
FIG. 6: Interaction plots for reactive oxygen species (ROS) fluorescence assay.
Figure 7:
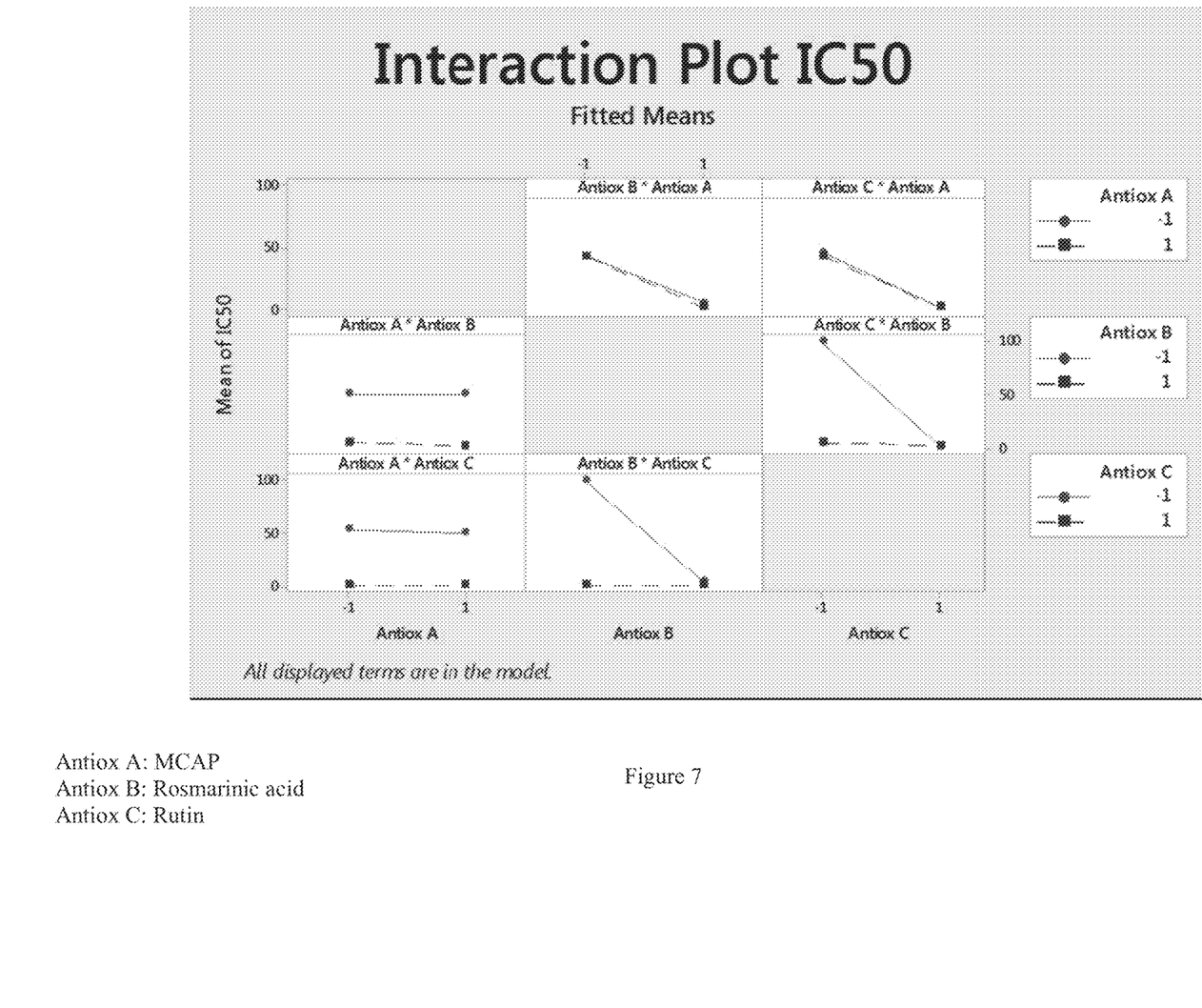
FIG. 7: Interaction plots for IC50 assay.
Figure 8:
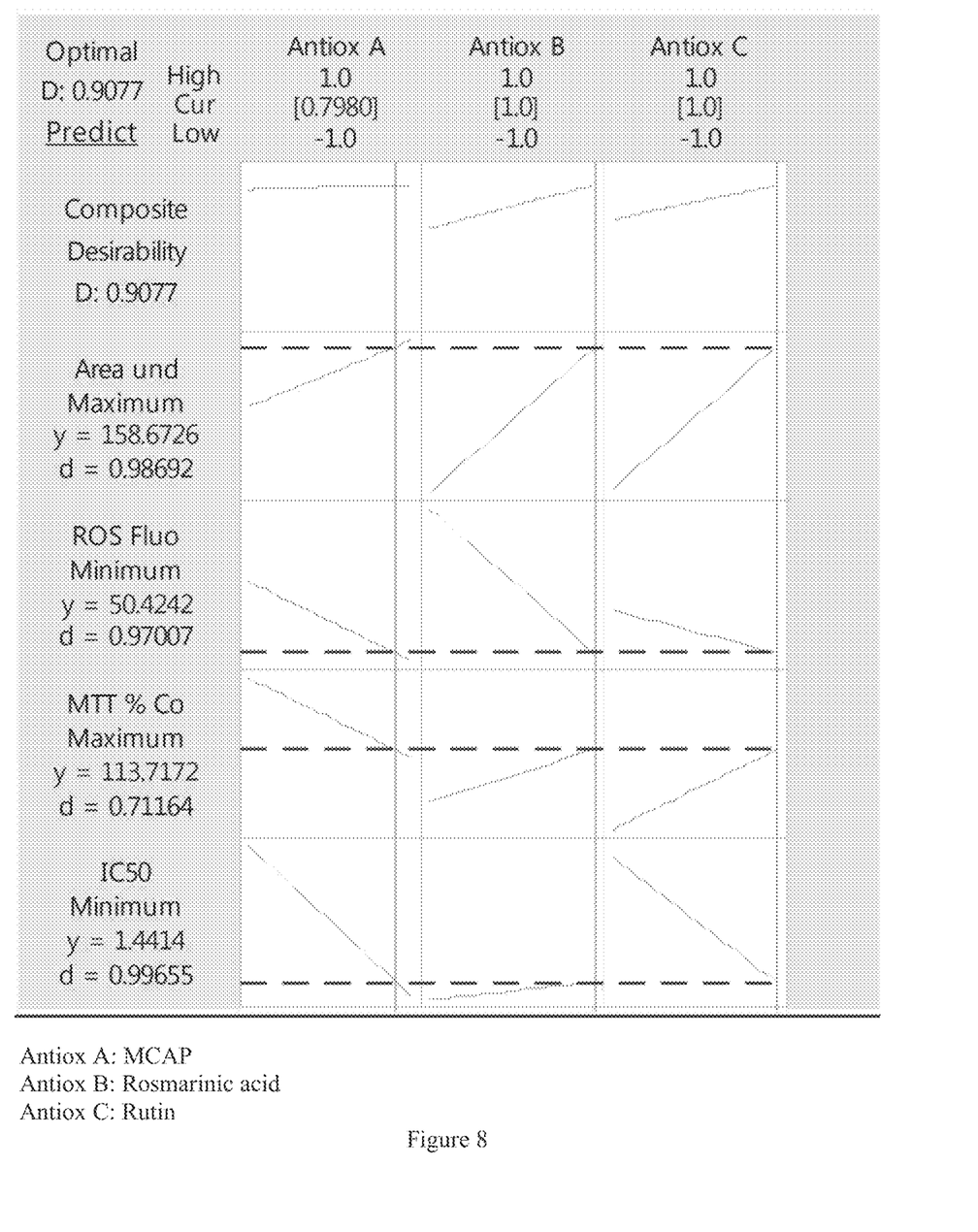
FIG. 8: Optimization plot in order to minimize IC50, maximize fibroblastmetabolic activity, minimize intracellular ROS, and maximize absorbance at 250-500 nm.

Experimental results indicated various synergies between MCAP, rosmarinic acid, and rutin. See FIGS. 1-7. The data from these experiments was used to create an optimized antioxidant composition of these three antioxidants. The optimized, multi-targeting composition provides a unique addition to various cosmetic formulations to provide various antiaging and photoprotective benefits Optimization plot indicates that rosmarinic acid and rutin are most important contributing molecules, while lower than tested levels of MCAP are theorized to maximize efficacy. See FIG. 8.

Example 1: Compositions of Ex1-Ex8

Compositions for Ex1-Ex8 have been used as DOE test articles in order to determine possible synergistic effects.

TABLE 1

Compositions of Ex1-Ex8.

| Function | INCI | Ex1 | Ex2 | Ex3 | Ex4 | Ex5 | Ex6 | Ex7 | Ex8 |
|---|---|---|---|---|---|---|---|---|---|
| Antioxidant | MCAP[1] | 0.0000 | 0.0030 | 0.0030 | 0.0030 | 0.0000 | 0.0000 | 0.0030 | 0.0000 |
|  | RA[2] | 0.3000 | 0.0000 | 0.0000 | 0.3000 | 0.0000 | 0.3000 | 0.3000 | 0.0000 |
|  | RU[3] | 0.3000 | 0.3000 | 0.0000 | 0.0000 | 0.3000 | 0.0000 | 0.3000 | 0.0000 |
| Solvent | PG[4] | 99.4000 | 99.400 | 99.700 | 99.400 | 99.700 | 99.700 | 99.100 | 100.000 |
|  | BG[5] | 0.0000 | 0.2940 | 0.2940 | 0.2940 | 0.0000 | 0.0000 | 0.2940 | 0.0000 |
|  | DW[6] | 0.0000 | 0.0030 | 0.0030 | 0.0030 | 0.0000 | 0.0000 | 0.0030 | 0.0000 |
|  | Total | 100.000 | 100.000 | 100.000 | 100.000 | 100.000 | 100.000 | 100.000 | 100.000 |

[1]Trade Name: Methyl Carboxymethylphenyl Aminocarboxy Propylphosphonate. Supplier: Kyoto. Lot number 160901
[2]Trade Name: Rosmarinic Acid ("RA"). Supplier: Sabinsa. Lot number C1311139-901
[3]Trade Name: Biotive Rutin ("Ru") Trihydrate. Supplier: Symrise. Lot number 10300003
[4]Trade Name: Pentylene Glycol ("PG"). Supplier: Symrise. Lot number 10300838
[5]Butylene Glycol ("BG")
[6]Deionized Water ("DW")

Example 2: Individual Antioxidant Data

MCAP, rosmarinic acid, and rutin have been tested for their activity, using Test Method A (DPPH), Test Method C (DCFH), and Test Method B (PHTX). Table 2 provides results of these experiments.

TABLE 2

Individual antioxidant data

| Antioxidant | DPPH Results (extracellular antioxidant) | DCFH Results (intracellular antioxidant) | PHTX Results |
|---|---|---|---|
| MCAP | No activity | +29% radial activity (pro-oxidant) | 22% more protective against UVA than solvent, not phototoxic |
| Rosmarinic acid | 0.0267% scavenges 50% radicals | −52% radical activity (antioxidant) | not phototoxic |
| Rutin | 0.0033% scavenges 50% radicals | No Activity | not phototoxic |

Example 3: Antioxidant Composition Tests

Compositions of Ex1-Ex8 have been tested for inhibitory concentrations yielding 50% inhibition of free radical 2,2- diphenyl-1-picrylhydrazyl) as determined by the Test Method A and presented in Table 3. Additional data is also presented in Table 4.

TABLE 3

IC50s of free radical 2,2-diphenyl-1-picrylhydrazyl for the composition of Ex1-Ex8.

| Example | IC50, v/v | Concentrations (wt %) of individual molecules corresponding to IC50 | Ratio of components corresponding to IC50 |
|---|---|---|---|
| Ex1 | 2.7 | RA (0.0081) RU (0.0081) MCAP (0) | 1 RA: 1 RU: 0 MCAP |
| Ex2 | 1.3 | RA (0) RU (0.0039) MCAP (0.000039) | 0 RA: 100 RU: 1 MCAP |
| Ex3 | Not active | Not applicable | Not applicable |
| Ex4 | 1.9 | RA (0.0057) RU (0) MCAP (0.000057) | 100 RA: 0 RU: 1 MCAP |
| Ex5 | 1.1 | RA (0) RU (0.0033) MCAP (0) | RU only |
| Ex6 | 8.9 | RA (0.0267) RU (0) MCAP (0) | RA only |
| Ex7 | 1.3 | RA (0.0039) RU (0.0039) MCAP (0.000039) | 100 RA: 100 RU: 1 MCAP |
| Ex 8 (Solvent) | Not applicable (Solvent) | Not applicable (Solvent) | Solvent only |

TABLE 4

Additional data for the composition of Ex1-Ex8.

| Example | Conc. of individual molecules in Human Dermal Fibroblasts, % of all blends = 0.1% | Conc. of individual molecules X10 assumption - for safe conc. on skin - topically, % | Conc. of individual molecules X100 assumption - for safe conc. on skin - topically, % | Directional metabolic activity increase after UVA Irradiation (OECD 432) VS. Non-irradiated, % | Effects on the UVA-induced Reactive Oxygen Species in Human Dermal Fibroblasts, % water control (note*$p < 0.05$) |
|---|---|---|---|---|---|
| Ex1 | RA (0.0003) RU (0.0003) MCAP (0) | RA (0.003) RU (0.003) MCAP (0) | RA (0.03) RU (0.03) MCAP (0) | +24 | 72 |
| Ex2 | RA (0) RU (0.000003) MCAP (0.0003) | RA (0) RU (0.00003) MCAP (0.003) | RA (0) RU (0.0003) MCAP (0.03) | +15 | 93 |
| Ex3 | RA (0) RU (0) MCAP (0.000003) | RA (0) RU (0) MCAP (0.00003) | RA (0) RU (0) MCAP (0.0003) | +35 | 129* |
| Ex4 | RA (0.0003) RU (0) MCAP (0.000003) | RA (0.003) RU (0) MCAP (0.00003) | RA (0.03) RU (0) MCAP (0.0003) | −2 | 65* |
| Ex5 | RA (0) RU (0.0003) MCAP (0) | RA (0) RU (0.003) MCAP (0) | RA (0) RU (0.03) MCAP (0) | +4 | 103* |
| Ex6 | RA (0.0003) RU (0) MCAP (0) | RA (0.003) RU (0) MCAP (0) | RA (0.03) RU (0) MCAP (0) | +18 | 48* |
| Ex7 | RA (0.0003) RU (0.0003) MCAP (0.000003) | RA (0.003) RU (0.003) MCAP (0.00003) | RA (0.03) RU (0.03) MCAP (0.0003) | +54 | 48* |
| Ex 8 (Solvent) | 0 | 0 | 0 | −5 | 98 |

Ex4 demonstrates a synergy between MCAP and Rosmarinic Acid, with a lower IC50 of 1.9 compared to MCAP alone, which is inactive (Ex. 3), and rosmarinic acid alone with an IC50 of 8.9 (Ex. 6). Rutin has the largest effect as an individual component in this assay as shown in Ex. 5.

Compositions of Ex1-Ex8 have been tested for the effects on cell viability pre- and post-UVA irradiation. The cell viability was measured by determining the cells metabolic activity with a MTT assay according to Test Method B, the results are presented in Table 5. An MTT assay is a colorimetric assay for assessing cell metabolic activity.

TABLE 5

Effects of compositions of Ex1-Ex8 on cell viability pre- and post-UVA irradiation.

| Example | MTT % of Control (−UVA) | MTT % of Control (+UVA) |
|---|---|---|
| Ex1 | 97 | 129 |
| Ex2 | 83 | 105 |
| Ex3 | 76 | 122 |
| Ex4 | 95 | 99 |
| Ex5 | 73 | 82 |
| Ex6 | 52 | 76 |
| Ex7 | 46 | 112 |
| Ex 8 (Solvent) | 100 | 100 |

The result of the antioxidant composition Ex1 indicate there is a synergy between rutin and rosmarinic acid in the UV-irradiation assay. Individually, rutin and rosmarinic acid have lower cell metabolism than solvent control, while Ex1 with rutin and rosmarinic acid results in 129% metabolic activity compared to solvent control. MCAP alone has the largest effect of an individual antioxidant in this assay as shown in Ex3. The tested materials were non phototoxic when tested up to 1 mg/ml, which is 10× higher than the normally tested highest concentration of 100 μg/ml.

Compositions of Ex1-Ex8 have been tested for reactive oxygen species quantification in UVA-irradiated human dermal fibroblasts. The quantification result is expressed as a percentage of the water control and determined by the Test Method C and presented in Table 6.

TABLE 6

Reactive oxygen species quantification of compositions of Ex1-Ex8 in UVA-irradiated human dermal fibroblasts.

| Example | ROS fluorescence compared to water control (%) |
|---|---|
| Ex1 | 72 |
| Ex2 | 93 |
| Ex3 | 129 |

TABLE 6-continued

Reactive oxygen species quantification of compositions of Ex1-Ex8 in UVA-irradiated human dermal fibroblasts.

| Example | ROS fluorescence compared to water control (%) |
|---|---|
| Ex4 | 65 |
| Ex5 | 103 |
| Ex6 | 48 |
| Ex7 | 48 |
| Ex 8 (Solvent) | 98 |

ROS quantification data shows an unexpected finding that MCAP as shown in Ex3 is a pro-oxidant in this assay. However, MCAP's pro-oxidant activity can be negated in the presence of rutin and rosmarinic acid as shown in Ex7. Therefore, the antioxidant composition unexpectedly mitigates the potentially negative side-effects of MCAP. Rosmarinic Acid has the largest effect of an individual antioxidant in this assay.

The absorbance of compositions of Ex1-Ex8 were measured according to Method D. See FIG. 2. Area under the curve between 250-500 nm represents absorbance in UVA, UVB, and blue light regions, while 400-500 nm represents absorbance in solely blue light region. Areas under the curve were determined by the Test Method D and calculated based on blank-corrected curves from Ex8, the solvent. Results presented in Table 7. The absorbance data demonstrated the synergistic effect of an increase in absorbance of light at 250-400 nm. The total amount of the increased absorbance is significantly more than the absorbance of any of the MCAP, the rosmarinic acid, the rutin alone. The increase of light absorbance at 250-400 nm is statistically significant.

TABLE 7

Area under curve of light absorbance for compositions of Ex1-Ex8.

| Example | Area under curve 250-500 nm | Area under curve 400-500 nm |
|---|---|---|
| Ex1 | 139.9538 | 1.22461 |
| Ex2 | 112.4022 | 1.89166 |
| Ex3 | No Absorbance | No Absorbance |
| Ex4 | 114.5675 | No Absorbance |
| Ex5 | 113.8896 | 1.74714 |
| Ex6 | 106.3731 | No Absorbance |
| Ex7 | 160.7758 | 1.22918 |

Figure 9:
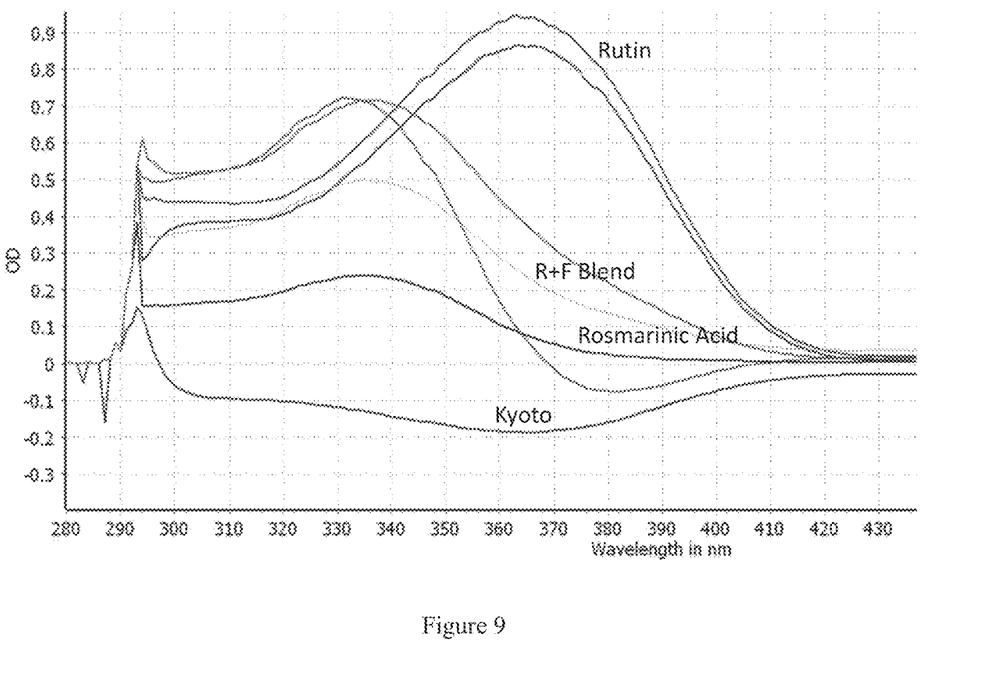
FIG. 9: Spectral data for MCAP, rosmarinic acid and rutin each individually and blend of three components.

The antioxidant blend of MCAP, rosmarinic acid, and rutin has been tested for synergistic activity compared with the results of individual components as presented in Example 2 and Table 2, using Test Method A (DPPH), Test Method C (DCFH), and Test Method B (PHTX). Table 8 and FIG. 9 provides results of these experiments.

TABLE 8

Results for antioxidant blend

| Antioxidant Blend | DPPH Results (extracellular antioxidant) | DCFH Results (intracellular antioxidant) | PHTX Results |
|---|---|---|---|
| 0.30% Kyoto solution, 0.30% Rosmarinic Acid, 0.30% Rutin in Pentylene glycol | 1.3% of blend scavenges 50% of radicals | −52% radical activity (antioxidant) | 12% more protection against UVA than solvent, Not phototoxic |

Example 4: Laboratory Testing Methods

Test Method A:
Example formulas were serially diluted and incubated with 100 μL of 2,2-diphenyl-1-picrylhydrazyl (DPPH) in triplicate. Reduction of absorbance at 520 nm was standardized to water control as an indication of DPPH-scavenging. Estimated IC50 values were extrapolated for the tread line equation of the graph (% inhibition) vs. ([test material]). Ascorbic acid was used as a positive control to validate the assay.

Test Method B:
Adult human fibroblasts were grown to exponential stage in a 96-well plate in DMEM and 10% FBS in humidified atmosphere, 37° C. in 5% CO2. Prior to irradiation, half of cell culture medium was replaced with PBS, treated with 0.1% test material (diluted in double distilled water), and incubated for an additional 1 hour 45 minutes. Following incubation, half of the plate was irradiated with UVA lamp UVA-28T at 5 mW/cm2 for 12 minutes, and the other half remained covered with aluminum foil. Following irradiation, PBS with test materials was replaced by fresh cell culture medium and plate was incubated for an additional 24 hours. Cell viability was then analyzed via MTT assay to quantify metabolic activity.

Test Method C:
Adult human fibroblasts were grown in a 96 well plate in DMEM+5% FBS. At exponential growth stage, medium was replaced with PBS and cells were loaded with 10 M DCFH-DA (2'-7'-Dichlorofluorescin diacetate). Cells were incubated for 15 minutes at 37° C., rinsed, and incubated with test materials at 1 mg/ml (0.1% w/w) for an additional 20 minutes. Following incubation, plate was irradiated at 5 mW/cm2 for 10 minutes. Measurements of DCF-originated fluorescence were taken before and after irradiation as, in the presence of free radicals, DCFH is oxidized to highly fluorescent DCF, which can be detected in living cells at ex/em 488/530 nm. Total insoluble proteins were quantified to determine effect of test materials on cell number and to standardize ROS signal to cell number using the following equation:

$$[\Delta ROS\ signal(t10\ min - t0)]\backslash[cell\ number(background-corrected)].$$

Water was used as a negative control.

Test Method D:
The antioxidant compositions were diluted to 2% in pentylene glycol. Absorbance was measured using a disposable 1.5 mL cuvette with the Ocean Optic UVis Spectrometer (slit width 10 L) to determine range of absorbance within UVB (290-320 nm), UVA (320-400 nm), blue light (400-490 nm), and near-vis (340-400 nm) ranges. The antioxidant compositions were blanked with pentylene glycol before measurement.

Test Method E:
Design of experiments were constructed and analyzed in MiniTab 17 Statistical Software using a full-factorial model. Data from previously described test methods was analyzed using optimization plots and interaction plots in order to both optimize formula for performance and to determine relationship between test materials, wherein an interaction plot displaying non-parallel lines indicates an interaction between factors.

Example 5: Press-Powder Formulation

The antioxidant compositions could be incorporated in the binder phase of press-powders, as in the following table:

| INCI | % w/w |
| --- | --- |
| Coco-Caprylate/Caprate | 2.0000-4.0000 |
| 1,2-Hexanediol | 0.5000-1.0000 |
| Caprylyl Glycol | 0.2500-0.5000 |
| Octyldodecyl Stearoyl Stearate | 1.5000-3.0000 |
| Rosmarinic Acid | 0.0010-0.0020 |
| Rutin | 0.0010-0.0020 |
| MCAP | 0.0010-0.0020 |

Combine Coco-Caprylate/Caprate, Octyldodecyl Stearoyl Stearate 1,2-Hexanediol and Caprylyl Glycol in the vessel.

Heat to 75° C. with adequate mixing. When composition reaches 75° C. add Rutin and Rosmarinic Acid.

Continue mixing until dissolved. Once dissolved begin cooling to room temperature with mixing.

Once temperature is below 30° C. add MCAP, mix until uniform. Combine with remaining formula ingredients (added up to 100.0000%).

Remaining ingredients of press powder may include: Mica, Kaolin, Synthetic Fluorphlogopite, Titanium Dioxide, Zinc Oxide, Silica, Barium sulfate, Nylon-12, Talc, Zinc stearate, Dimeticone, Tocopheryl acetate, Stearic acid, Boron Nitride, Dimethicone, Lauroyl Lysine, Methyl Methacrylate Crosspolymer, Stearic Acid, Plant Extracts, Preservative (e.g. Phenoxyethanol); Also may contain: Iron Oxides (Ci 77489, Ci 77491, Ci 77492, Ci 77499), Ultramarines (Ci 77007), Chromium Oxide Greens (Ci 77288).

Example 6: Pickering Emulsion Formulation

The antioxidant compositions could be incorporated in Pickering emulsion, as in the following table:

| Phase | INCI | % w/w |
| --- | --- | --- |
| A | Water | a.d. 100.0000 |
| | Glycerin | 10.0000 |
| | Butylene Glycol | 2.0000 |
| | Rosmarinic Acid | 0.0010 |
| | Rutin | 0.0010 |
| | Hydrated Silica | 2.0000 |
| | Preservative: Phenylpropanol (and) propanediol (and) caprylyl glycol (and) tocopherol | 1.0000 |
| B | Silica cetyl silylate | 2.0000 |
| C | Caprylic/Capric Triglyceride | 8.0000 |
| | Diethylhexyl carbonate | 6.0000 |
| | Isoamyl cocoate | 4.0000 |
| | Tocopheryl Acetate | 0.2000 |
| | Xanthan Gum | 0.2000 |
| D | MCAP | 0.0010 |
| | Fragrance | q.s. |

Combine Phase A ingredients with sufficient agitation.

Mix until Rosmarinic Acid and Rutin are fully dissolved and system is uniform. If necessary, phase could be heated to 45-50° C. (to expedite the dissolution process).

Add Phase B ingredient slowly to water phase with gentle agitation until it is fully incorporated and system is uniform. Homogenize under vacuum.

In separate vessel combine Phase C ingredients and mix until uniform with moderate agitation, until Xanthan Gum is dispersed.

Add Phase C to combined Phases A and B, with moderate agitation and homogenize.

Add MCAP with moderate agitation once the temperature is below 30° C.

The disclosures of each and every patent, patent application, publication, and accession number cited herein are hereby incorporated herein by reference in their entirety.

While present disclosure has been disclosed with reference to various embodiments, it is apparent that other embodiments and variations of these may be devised by others skilled in the art without departing from the true spirit and scope of the disclosure. The appended claims are intended to be construed to include all such embodiments and equivalent variations.

The invention claimed is:

1. An antioxidant composition comprising: methyl carboxymethylphenylaminocarboxy propylphosphonate (MCAP),
    (2R)-3-(3,4-dihydroxyphenyl)-2-{[(2E)-3-(3,4-dihydroxyphenyl)prop-2-enoyl]oxy}propanoic acid (rosmarinic acid), and
    2-(3,4-dihydroxyphenyl)-5,7-dihydroxy-3-[α-L-rhamnopyranosyl-(1→6)-β-D-glucopyranosyloxy]-4H-chromen-4-one (rutin),
    wherein the ratio of the MCAP: the rosmarinic acid: the rutin in the antioxidant composition is about 1:100:100.

2. The antioxidant composition of claim 1, wherein the antioxidant composition demonstrates a synergistic effect compared with the MCAP, the rosmarinic acid, or the rutin, alone.

3. The antioxidant composition of claim 1, wherein the MCAP is present in the antioxidant composition in an amount of about 0.0001 wt. % to about 1.0 wt. %.

4. The antioxidant composition of claim 1, wherein the rosmarinic acid is present in the antioxidant composition in an amount of about 0.0001 wt. % to about 1.0 wt. %.

5. The antioxidant composition of claim 1, wherein the rutin is present in the antioxidant composition in an amount of about 0.0001 wt. % to about 1.0 wt. %.

6. The antioxidant composition of claim 2, wherein the synergistic effect is an increase in absorbance of light at 250-400 nm.

7. The antioxidant composition of claim 6, wherein the total amount of the increased absorbance is significantly more than the absorbance of any of the MCAP, the rosmarinic acid, or the rutin alone.

8. A topical formulation comprising the antioxidant composition of claim 1.

9. The topical formulation of claim 8, wherein the topical formulation further comprising a solvent.

10. The topical formulation of claim 9, wherein the solvent is selected from the group consisting of pentylene glycol, butylene glycol, water, ethanol, and combinations thereof.

11. The topical formulation of claim 8, wherein the total amount of the antioxidant composition in the topical formulation is about 0.000001 wt. % to about 5.0 wt. %.

12. The topical formulation of claim 8, wherein the topical formulation further comprises a pharmaceutical additive, a cosmetic additive, water, or combinations thereof.

13. The topical formulation of claim 12, wherein the pharmaceutical additive is selected from the group consisting of diluents, fillers, disintegrants, binders, lubricants, surfactants, hydrophobic vehicles, water soluble vehicles, emulsifiers, buffers, humectants, moisturizers, solubilizers, preservatives, colorants, plasticizers, carriers, excipients, and combinations thereof.

14. The topical formulation of claim 12, wherein the cosmetic additive is selected from the group consisting of vitamins, cosmetic peptides, oil control agents, sensation modifying agents, skin lightening agents, hydrating formulations, a sunblock agent, a compound that absorbs or reflects UV photons, other skin care agent and combinations thereof.

15. The topical formulation of claim 8, wherein the topical formulation is formulated in a form selected from the group consisting of a solution, fluid, emulsion, suspension, solid, semi-solid, jelly, paste, gel, hydrogel, ointment, lotion, emulsion, cream, foam, mousse, liquid, spray, suspension, dispersion, powder, aerosol, color cosmetic, hair treatment, scalp care product, or transdermal patch.

16. A method of treating skin damage by reactive oxygen species in a subject in need thereof comprising topically administering to the skin of the subject an antioxidant composition comprising:
    methyl carboxymethylphenylaminocarboxy propylphosphonate (MCAP),
    (2R)-3-(3,4-dihydroxyphenyl)-2-{[(2E)-3-(3,4-dihydroxyphenyl) prop-2-enoyl]oxy}propanoic acid (rosmarinic acid), and
    2-(3,4-dihydroxyphenyl)-5,7-dihydroxy-3-[α-L-rhamnopyranosyl-(1→6)-β-D-glucopyranosyloxy]-4H-chromen-4-one (rutin),
    wherein the ratio of the MCAP: the rosmarinic acid: the rutin in the antioxidant composition is about 1:100:100.

17. The method of claim 16, wherein the antioxidant composition demonstrates a synergistic effect compared with the MCAP, the rosmarinic acid, or the rutin alone.

18. The method of claim 16, wherein the subject is an infant, a child, an adolescent, or an adult.

19. The method of claim 16, wherein the skin damage is damage to lipids, proteins, DNA, or combinations thereof.

20. The method of claim 16, wherein the reactive oxygen species is generated by UV radiation, pollution, heating, or combinations thereof.

21. A method of improving the appearance of aged skin in a subject in need thereof comprising topically administering to the skin of the subject an antioxidant composition comprising: methyl carboxymethylphenylaminocarboxy propylphosphonate (MCAP),
    (2R)-3-(3,4-dihydroxyphenyl)-2-{[(2E)-3-(3,4-dihydroxyphenyl) prop-2-enoyl]oxy}propanoic acid (rosmarinic acid), and
    2-(3,4-dihydroxyphenyl)-5,7-dihydroxy-3-[α-L-rhamnopyranosyl-(1→6)-β-D-glucopyranosyloxy]-4H-chromen-4-one (rutin),
    wherein the ratio of the MCAP: the rosmarinic acid: the rutin in the antioxidant composition is about 1:100:100.

22. The method of claim 21, wherein the antioxidant composition demonstrates a synergistic effect compared with the MCAP, the rosmarinic acid, or the rutin alone.

23. The method of claim 21, wherein the characteristic of the skin is selected from the group consisting of firmness, elasticity, fine lines, wrinkles, skin texture, skin tone, appearance, and any combination thereof.

24. The method of claim 21, wherein improving the appearance of the skin results in smoother skin, firmer skin, brighter complexion, improved texture of the skin, even-looking skin, or younger-looking skin.

25. The method of claim 21, wherein improving the appearance of the skin results in an increase in elasticity of the skin, a decrease in the fine lines of the skin, a decrease in the wrinkles of the skin, a more consistent skin tone, and any combination thereof.

* * * * *